United States Patent [19]
Little et al.

[11] Patent Number: 5,919,684
[45] Date of Patent: Jul. 6, 1999

[54] PROCESS FOR THE REDUCTION OF CATALASE ACTIVITY IN ALCOHOL OXIDASE

[75] Inventors: Tina M. Little, Pearland, Tex.; Wayne W. Fish, Bartlesville, Okla.

[73] Assignee: Moldowan Lab Inc., Philomath, Oreg.
This patent issued on a continued prosecution application filed under 37 CFR 1.53(d), and is subject to the twenty year patent term provisions of 35 U.S.C. 154(a)(2).

[21] Appl. No.: 07/667,166

[22] Filed: Mar. 11, 1991

[51] Int. Cl.$^6$ ................ C12N 9/04; C12N 9/08
[52] U.S. Cl. ............ 435/190; 435/71.1; 435/192; 435/816; 435/938
[58] Field of Search .................... 435/190, 192, 435/71.1, 938, 816

[56] References Cited

U.S. PATENT DOCUMENTS

| | | | |
|---|---|---|---|
| 4,421,668 | 12/1983 | Cox et al. | 252/174.12 |
| 4,540,668 | 9/1985 | Hopkins et al. | 435/190 |
| 4,617,274 | 10/1986 | Wegner | 435/255 |
| 4,619,898 | 10/1986 | Hopkins | 435/190 |

FOREIGN PATENT DOCUMENTS

| | | | |
|---|---|---|---|
| 0173378 | 5/1986 | European Pat. Off. | C12N 15/00 |
| 244920 | 2/1987 | European Pat. Off. | C12N 9/04 |
| 242007 | 5/1987 | European Pat. Off. | C12N 9/04 |

*Primary Examiner*—Ponnathapura Achutamurthy

[57] ABSTRACT

A process is disclosed for treating compositions of alcohol oxidase to inactivate catalase therein, which comprises aging the composition comprising alcohol oxidase and catalase at a temperature and for a time period sufficient to inactivate catalase while maintaining the alcohol oxidase activity.

16 Claims, No Drawings

PROCESS FOR THE REDUCTION OF CATALASE ACTIVITY IN ALCOHOL OXIDASE

This invention relates to a novel process for reducing catalase activity in compositions comprising alcohol oxidase and catalase.

BACKGROUND

Alcohol oxidases are known to be produced by various microorganisms grown on methanol. These alcohol oxidases catalyze the reaction $$RCH_2OH + O_2 \rightarrow RCHO + H_2O_2$$

where R is hydrogen or a lower alkyl. Alcohol Oxidases can be used to remove oxygen from compatible solutions, as well as be used in the production of aldehydes (RCHO) and hydrogen peroxide ($H_2O_2$). Where R represents the methyl group ($CH_3$), alcohol oxidase is the enzyme that catalyzes the oxidation of methanol to formaldehyde and hydrogen peroxide.

The production of $H_2O_2$ with alcohol oxidase is often desirable since such peroxide has application in bleaching components of detergents and the like. However, one problem in the production of alcohol oxidase from yeast extracts is that catalase levels remain significant in the extract. Catalase breaks down $H_2O_2$ into water and oxygen, thus, seriously impairing potential uses of the alcohol oxidase extract.

Presently, when a production lot of alcohol oxidase is high in amount of catalase activity, i.e., has retained more than 10 percent of its original catalase activity, such a lot is unacceptable for commercial use and is discarded. The high level of catalase activity is represented by about 20 percent of the alcohol oxidase lots presently produced, hence, approximately one in every five is unacceptably high in catalase activity. Therefore, a method which would enable reduction of the catalase activity in the lots of alcohol oxidase originally high in catalase activity would thus permit the alcohol oxidase to be used rather than discarded and would therefore represent a significant contribution to the art.

SUMMARY OF THE INVENTION

It is therefore an object of this invention to provide a method for reducing catalase activity in alcohol oxidase compositions.

These and other objects of the present invention will become apparent from inspection of the disclosure and claims herein provided.

DETAILED DESCRIPTION

In accordance with the present invention, there is provided a method for reducing catalase activity of alcohol oxidase obtained from *Pichia pastoris* which comprises aging the alcohol oxidase at a temperature and for a time period sufficient to essentially inactivate catalase while not significantly affecting the activity of alcohol oxidase. "Inactivate" as used herein describes a process whereby enzyme activity is irreversibly decreased.

The term "aging" as used herein refers to a process whereby prepared alcohol oxidase is stored at a temperature and for a time period such that catalase present in the alcohol oxidase is inactivated. In carrying out the aging of the present invention, a temperature in the range of about 1° C. to about 15° C. for a time period for at least 20 days, are conditions which are preferred. Most preferable conditions are a temperature of about 4° C. for a time period of 60 days. The aging process can be performed on alcohol oxidase compositions ranging in degree of purity, and the effect of the aging conditions on each varies slightly as detailed infra. Nonetheless, when the conditions of aging are met, the alcohol oxidase retains virtually all of its original activity while catalase is almost entirely inactivated.

In carrying out the process of the present invention, there is employed a suspension of *Pichia pastoris* cells from which is derived the alcohol oxidase to be treated in accordance with the present invention. *Pichia pastoris* yeast used in the practice of the present invention is capable of utilizing methanol as a source of carbon and energy.

Two preferred suitable strains of the species *Pichia pastoris* are those which have been deposited with the United States Department of Agriculture, Agriculture Research Service, Northern Regional Research Laboratories of Peoria, Ill., and designated NRRL Y-11430 and Y-11431.

According to the present invention, a selected strain of methanol competent *Pichia pastoris* is cultured under aerobic aqueous fermentation conditions using methanol as the carbon and energy source. Preferably the methanol is supplied under conditions such that methanol is the growth-limiting factor. The methanol limiting factor is that concentration of methanol which is the minimal concentration of methanol which results in a maximum growth rate for a given set of fermentation culture conditions. Preferably fermentation is conducted under high cell density conditions, such that the cell density in the fermentor is 50 grams or greater on a dry weight basis per liter of ferment. The selected yeast can be grown in a batch or continuous process in the presence of oxygen, methanol, and an assimilable source of nitrogen. Various types of fermentation processes and apparatuses known in the art can be utilized. The presently preferred fermentation is described in Wegner, U.S. Pat. No. 4,617,274, issued on Oct. 14, 1986 and assigned to Phillips Petroleum Company.

In carrying out the fermentation of *Pichia pastoris,* oxygen, water and pressure conditions are as follows. Oxygen can be supplied to the fermenter as such, or in the form of air or oxygen-enriched air, in a range of pressures from such as about 0.1 atm. to 100 atm., as is known in the art. The assimilable source of nitrogen for the fermentation can be any organic or inorganic nitrogen containing compound which provides nitrogen in a form suitable for metabolic utilization by the microorganisms. Suitable organic nitrogen sources include, for example, proteins, amino acids, urea, and the like. Suitable inorganic nitrogen sources include, for example, ammonia, ammonium hydroxide, ammonium nitrate, and the like. The presently preferred nitrogen sources includes ammonia end ammonium hydroxide for convenience and availability.

Sufficient water is maintained in the fermentor so as to provide for the particular requirements of the microorganisms employed as well as to provide a carrier fluid for water soluble nutrients. Minerals, growth factors, vitamins, and the like, generally are added in amounts which vary according to the strain of microorganisms utilized and the selected culture conditions, and are known to those skilled in the art or are readily determinable by them. A suitable nutrient medium is set forth below in Example 1.

Fermentation pressures are generally within the range of about 0.1 to about 100 atmospheres, more usually about 1 to about 30 atmospheres, and more preferably about 1 to about 5 atmospheres since the higher pressures result in a greater level of dissolved oxygen in the aqueous medium and usually higher cell productivities.

As presently practiced, the fermented cells of *Pichia pastoris* are lysed. Lysing of the yeast cells may be performed using methods known to those of ordinary skill in the art. These methods include but are not limited to physical methods such as the utilization of bead mills as well as chemical methods such as with diethyl either or methylene chloride. Presently preferred is a chemical method utilizing methylene chloride.

Cell debris from the lysed cells is preferably removed after lysing. Removal of cell debris entails separating the soluble fraction containing alcohol oxidase and catalase from the resulting solid material which comprises cell debris formed by the lysis process. Separation may be accomplished by any methods known to those skilled in the art. Such methods include but are not limited to centrifugation and filtration.

After removal of cell debris, the resulting alcohol oxidase is in a crude composition which can undergo successful aging in accordance with this invention. However, further treatment to increase the purity of the alcohol oxidase provides products which can also undergo successful aging.

A composition of intermediate purity is prepared by ammonium sulfate fractionation as described in Example 3. Aging this alcohol oxidase composition successfully inactivates catalase while retaining alcohol oxidase activity.

A further purified composition results when crystallization is performed after removal of cell debris of the first crude composition. As presently practiced, crystallization is performed in accordance with the procedure disclosed in Hopkins, U.S. Pat. No. 4,540,668, issued on Sep. 10, 1985, and assigned to Phillips Petroleum Company.

Crystalline alcohol oxidase for use in the present invention is prepared by treatment of lysed Pichia cells under dialysis conditions either by conventional dialysis modes or by applying ultrafiltration to increase the rate of recovering soluble material. The solution resulting from lysing of Pichia cells and the subsequent removal of insolubles material and which contains the soluble alcohol oxidase is dialyzed against a dialysis medium across a membrane impermeable to alcohol oxidase but permeable to water, buffer, and inorganic molecules. The dialysis medium can be any medium whereby during dialysis, the molar ionic strength of the solution on the enzyme side of the membrane equilibrates is in a range between 0.05 M and 0.01 M thereby effecting precipitation of the alcohol oxidase.

During dialysis the pH of the alcohol oxidase containing solution is maintained in the range of pH of 6.0 to 6.5 by use of a suitable buffer. Such potassium dihydrogen phosphate and dipotassium hydrogen phosphate in combination with one another to produce the pH values in this range. The dialysis can be safely carried out at temperatures in the range of 4° C. to 37° C. The crystalline alcohol oxidase can be separated from the mother liquor by decantation or centrifugation. Crystalline precipitate is thereafter placed into a 0.05 M phosphate buffer to achieve a suspension.

Aging is successful whether performed on the crystalline suspension or on a solution achieved when crystallized alcohol oxidase is dissolved in an aqueous solution having a pH in a range of about 5.5 to about 8.5. As presently practiced, the aqueous solution is sucrose in a buffered solution having a sucrose concentration of 30% weight/volume.

Compositions of prepared alcohol oxidase are successfully aged regardless of the purity of the composition. Compositions range from crude products such as those prepared by fermenting *Pichia pastoris* yeast cells, lysing the cells and then removing cell debris to those more extensively purified compositions such as those prepared by crystallization following the removal of cell debris and placing the resulting crystalline precipitate in a phosphate buffer to achieve a suspension; or the composition formed by dissolving crystallized alcohol oxidase in an aqueous medium having a pH in a range of about 5.5 to about 8.5.

The minimal aging time period is about 20 days because at this point, catalase has been sufficiently inactivated so as to make the alcohol oxidase useful for its intended purposes. Once aging continues to the point where catalase is completely inactivated, the alcohol oxidase product can remain in storage at a temperature in the range of about 1° C. to about 15° C. for an indefinite period until utilized.

It is presently preferred that a preservative is added to an alcohol oxide composition prior to aging. This preservative acts as an antimicrobial agent and is selected from the group consisting of thymol and an azide. The preservative is added in an amount in the range of about 0.01 to about 0.1 percent total volume. The term azide as used herein refers to any salt of hydrozoic acid of electro-positive metals. Such metals are selected from the group consisting of Na, Ca, K, Mg and Li. A presently preferred azide is sodium azide.

EXAMPLES

The following examples are provided to illustrate the practice of the invention and are not intended to limit the scope of the invention or the appended claims in anyway.

Example 1

In a run conducted under continuous aerobic fermentation process conditions, methanol and an aqueous mineral salts medium in a volume ratio of 30.15 to 69.85, respectively, were fed individually to a fermentor inoculated with the yeast *Pichia pastoris* NRRL Y-11431. No pre-conditioning medium or substrate was employed. The fermentor was a 4-liter fermentor with a 2-liter liquid volume, with automatic pH, temperature, and level control. Agitation was provided by two impellers rotating at 1000–1200 rpm. The aeration rate was 1–1.5 volumes (at about atmospheric pressure and about 25° C.) per volume of ferment per minute of air supplemented with and including sufficient oxygen to maintain in the fermentation mixture an amount of dissolved oxygen equal to about 20 percent of that which would be dissolved in the fermentation mixture saturated with air at atmospheric pressure and about 30° C. Aqueous ammonium hydroxide (from 2 parts concentrated ammonium hydroxide and 1 part deionized water, by volume) was added at such a rate as to maintain the pH of the fermentation mixture at about 3.5.

The aqueous mineral salts medium employed was prepared by mixing, for each liter of solution, 12.5 mL 85 percent $H_3PO_4$ 2.5 g 85 percent KOH, 8.5 g KCl, 7.0 g $MgSO_4 \cdot 7H_2O$, 1.5 g $CaCl_2 2H_2O$, 25 mL of trace mineral solution A, 25 mL of trace mineral solution B, 10 mL of a biotin-thiamine hydrochloride solution, about 0.08 mL of antifoam agent (Mazu DF-37C), and sufficient deionized water to make 1 liter of solution.

Trace mineral solution A was prepared by mixing, for each liter solution, 4.8 g $FeCl_3 \cdot 6H_2O$, 2.0 g $ZnSO_4 \cdot 7-H_2O$, 0.02 g $H_3BO_3$, 0.20 g $Na_2MoO_4 \cdot 2H_2O$, 0.30 g $MnSO_4 \cdot H_2O$, 0.08 g KI, 0.06 g $CuSO_4 \cdot 5H_2O$, 3 ml conc. $H_2SO_4$, and sufficient deionized water to make 1 liter of solution.

Trace mineral solution B was prepared by mixing, for each liter of solution, 2.0 g $FeCl_3 6H_2O$, 2.0 g $ZnSO_4 \cdot 7-H_2O$, 0.3 g MnSO$_4$•H$_2$O, 0.6 g CuSO$_4$•5H$_2$O, 2 ml conc. H$_2$SO$_4$, and sufficient deionized water to make 1 liter of solution.

The biotin-thiamine hydrochloride solution was prepared by mixing 2 mg biotin, 200 mg thiamine hydrochloride, and 50 mL deionized water.

The fermentation was conducted at about 30° C. and at about atmospheric pressure, with a retention time of 7.0 hours.

Yeast cells were separated from the fermentation effluent by centrifugation, washed by suspension in water and recentrifugation, dried overnight at 100° C., and weighed. On a dried basis, the yeast cells were produced in a yield of 42.3 g per 100 g of methanol fed, the cell density being at the high level of 100.7 g of cells per liter of effluent.

Example 2

One liter of whole *Pichia pastoris* cells, obtained by a fermentation process as described in Example 1 were lysed for 6 days with methylene chloride at 10° C. in the presence of 0.02 percent NaN$_3$, and cell debris was removed by centrifugation. The supernatant contained among other things alcohol oxidase and catalase. The pH of the supernatant was adjusted to pH 7.5 by the addition of 1N KOH. The supernatant was then stored in a 10° C. cold box. The levels of alcohol oxidase as measured by the ABTS assay (Sahm, H. and Wagner, F. (1973) Eur. J. Biochom. 36, 250–256) and catalase as measured by the generation of O$_2$ with the use of a dissolved oxygen meter (Rorth, M. and Jensen, P. K. (1967) Biochem. Biophys. Acta 139, 171–173) were determined as a function of time of storage at 10° C. The initial (time=0) catalase activity was 13,683 units/ml and the initial alcohol oxidase activity was 93 units/ml.

The results of this study are presented in Table 1 the data of which demonstrates that even in the crudest state, i.e. as broken cell supernatant, *Pichia pastoris* alcohol oxidase retains most of its activity when stored at 10° C. over a two to three month interval while the *Pichia pastoris* catalase loses up to 95 percent of its original activity when treated in accordance with the present invention. The word "original" as used herein, refers to the amount of activity present in a composition just prior to aging.

TABLE I

Effect of Storing Crude Alcohol Oxidase at 10° C. on the Alcohol Oxidase and Catalase Activities

| Aging at 10° C. (Days) | Percent of Original Alcohol Oxidase Activity | Percent of Original Catalase Activity |
|---|---|---|
| 0 | 100 | 100 |
| 5 | 93 | 77 |
| 16 | 90 | 43 |
| 47 | 94 | 20 |
| 75 | 85 | 6 |

Example 3

One liter of whole *Pichia pastoris* cells, obtained by the fermentation process as described in Example 1 were lysed for 4 days with methylene chloride at 10° C. in the presence of 0.02 percent NaN$_3$, and cell debris was removed by centrifugation. The pH of the supernatant was adjusted to 7.5 with concentrated NH$_4$OH. Solid ammonium sulfate was added at room temperature with stirring to 40 percent saturation of ammonium sulfate (243 g (NH$_4$)$_2$SO$_4$ to 1 liter of supernatant). The pH was maintained at 7.5 with NH$_4$OH during ammonium sulfate addition. The suspension was centrifuged, the precipitate discarded, and solid ammonium sulfate was added to the supernatant with stirring to bring the final concentration of ammonium sulfate to 60 percent saturation (an additional 132 g (NH$_4$)$_2$SO$_4$ per 1 liter of supernatant). The suspension was centrifuged and the precipitate was saved. The precipitate contained, among other things, alcohol oxidase and catalase activities. The precipitate was dissolved in 15 ml of 30 percent sucrose plus 0.02 percent NaN$_3$ in 0.05 M potassium phosphate buffer, pH 7.5. The solution was stored at 4° C., and aliquots were assayed at intervals for alcohol oxidase activity and catalase activity. Alcohol oxidase was measured by the ABTS assay (Sahm, H. and Wagner, F. (1973) Eur. J. Biochem. 36, 250–256) and catalase was measured by the generation of O$_2$ with the use of a dissolved oxygen meter (Rorth, M. and Jensen, P. K. (1967) Biochem. Biophys. Acta 139, 171–173). The initial (time=0) catalase activity was 991,000 units/ml, and the initial alcohol oxidase activity was 6,473 units/ml.

The results are presented in Table 2 the data of which demonstrates that contaminating catalase activity in partially purified forms of *Pichia pastoris* alcohol oxidase prepared by ammonium sulfate fractionation can be markedly lowered by prolonged storage at 4° C.

TABLE II

Effect of Storing Partially Purified Alcohol Oxidase at 4° C. on the Alcohol Oxidase and Catalase Activities

| Aging at 4° C. (Days) | Percent of Original Alcohol Oxidase Activity | Percent of Original Catalase Activity |
|---|---|---|
| 0 | 100 | 100 |
| 3 | 97 | 83 |
| 17 | 91 | 7 |
| 46 | 85 | <1 |
| 76 | 81 | <1 |

Example 4

Eighty liters of whole *Pichia pastoris* cells, obtained by the fermentation process as described in Example 1 were lysed by bead milling. Cell debris was separated from the soluble material by diafiltration of the lysed cells (A. V. Quirk and J. R. Woodrow (1984) Enzyme and Microbial Technology 6, 201–206). The *Pichia pastoris* solubles were then dialyzed at pH 8.5 by applying ultrafiltration with a volume of deionized water three times that of the volume of *Pichia pastoris* solubles. This solution was then concentrated six-fold by ultra-filtration, the conductivity adjusted to 3 mSiemens/cm by the addition of Na$_2$SO$_4$, and the pH adjusted to 6.9 with 1N H$_3$PO$_4$. After holding at 10° C. for 18 hours, alcohol oxidase crystals were separated from the mother liquor by centrifugation. The crystals were suspended in an equal volume of 0.05 M potassium phosphate buffer, pH 7.5, equal to the volume of crystals present, thymol was added (as a preservative) to a concentration of 0.05 percent. The crystal slurry was stored at 4° C. and sampled periodically to measure alcohol oxidase and catalase activity levels. Alcohol oxidase was measured by the ABTS assay (Sahm, H. and Wagner, F. (1973) Eur. J. Biochem. 36, 250–256). Catalase was measured by the generation of O$_2$ with the use of a dissolved oxygen meter (Rorth, M. and Jensen, P. K. (1967) Biochem. Biophys. Acta 139, 171–173). The initial level of alcohol oxidase activity was 3,698 U/ml. The initial level of catalase activity was 2,900 U/ml.

The percentage of each enzymatic activity remaining as a function of length of storage at 4° C. is presented in Table 3 the data of which demonstrates that catalase activity in a production lot of crystalline *Pichia pastoris* alcohol oxidase can be significantly decreased by prolonged storage at 4° C. of a slurry of same in the presence of a preservative.

TABLE III

Effect of Storing Crystalline Alcohol Oxidase at 4° C. on the Alcohol Oxidase and Catalase Activities

| Aging at 4° C. (Days) | Percent of Original Alcohol Oxidase Activity | Percent of Original Catalase Activity |
| --- | --- | --- |
| 0 | 100 | 100 |
| 3 | 85 | 92 |
| 9 | 79 | 60 |
| 15 | 78 | 28 |
| 23 | 80 | 22 |
| 29 | 72 | 21 |
| 37 | 72 | 17 |
| 43 | 84 | 16 |

Reasonable variations and modifications, not departing from the essence and spirit of the invention, are contemplated to be within the scope and patent protection.

That which is claimed is:

1. A process for inactivating catalase in a composition comprising alcohol oxidase and catalase which comprises aging said composition obtained by the fermentation of *Pichia pastoris* cells at a temperature and for a time period sufficient to accomplish inactivating said catalase while maintaining alcohol oxidase activity.

2. A process in accordance with claim 1 wherein said composition comprising alcohol oxidase and catalase is prepared by fermenting *Pichia pastoris* cells, lysing the resulting cells and thereafter removing cell debris.

3. A process in accordance with claim 1 wherein said composition of alcohol oxidase, after said aging has occurred, is dissolved in an aqueous medium having a pH range of about 6.0 to about 8.5.

4. A process in accordance with claim 3 wherein said aqueous medium contains 30 percent weight/volume sucrose.

5. A process in accordance with claim 1 wherein said composition is prepared by fermenting *Pichia pastoris* cells, lysing the resulting cells, removing cell debris and thereafter crystallizing the alcohol oxidase and suspending the resulting crystalline precipitate comprising alcohol oxidase and catalase in a phosphate buffer.

6. A process in accordance with claim 5 wherein said crystallized and suspended alcohol oxidase is thereafter dissolved in an aqueous medium having a pH in a range of about 6.0 to about 8.5.

7. A process in accordance with claim 6 wherein said aqueous medium contains 30 percent weight/volume sucrose.

8. A process in accordance with claim 1 wherein a preservative is added to the composition prior to aging.

9. A process in accordance with claim 8 wherein said preservative is selected from the group consisting of an azide and thymol.

10. A process in accordance with claim 9 wherein said azide is a salt of hydrazoic acid-and an electro-positive metal.

11. A process in accordance with claim 10 wherein said electro-positive metal is selected from the group consisting of Na, Ca, K, Mg and Li.

12. A process in accordance with claim 9 wherein the azide is sodium azide.

13. A process in accordance with claim 8 wherein said preservative is added in an amount in the range of about 0.01 to about 0.1 percent (weight/volume).

14. A process in accordance with claim 1 wherein aging is carried out at a temperature in the range of about 1° C. to about 15° C. and said period of time is at least 20 days.

15. A process in accordance with claim 1 wherein aging is carried out at a temperature of about 4° C. and for a time period of about 40 days.

16. A process in accordance with claim 5 wherein the suspension of crystallized alcohol oxidase is treated with sodium azide in an amount in the range of about 0.01 to about 0.1 percent (weight/volume), and thereafter aged at a temperature of about 4° C. for a time period of about 40 days.

* * * * *